United States Patent [19]
Hart et al.

[11] Patent Number: 6,139,555
[45] Date of Patent: Oct. 31, 2000

[54] GRASPING CLIP APPLIER

[75] Inventors: Charles C. Hart, Huntington Beach; Donald L. Gadberry, Dana Point, both of Calif.

[73] Assignee: Applied Medical Resources Corporation, Rancho Santa Margarita, Calif.

[21] Appl. No.: 09/171,273

[22] PCT Filed: Apr. 17, 1997

[86] PCT No.: PCT/US97/06537

§ 371 Date: Oct. 15, 1998

§ 102(e) Date: Oct. 15, 1998

[87] PCT Pub. No.: WO97/39689

PCT Pub. Date: Oct. 30, 1997

Related U.S. Application Data

[60] Provisional application No. 60/015,625, Apr. 19, 1996.

[51] Int. Cl.[7] .................................................. A61B 17/10
[52] U.S. Cl. ......................... 606/139; 606/142; 606/143; 606/157
[58] Field of Search ................................... 606/138, 139, 606/142, 143, 157

[56] References Cited

U.S. PATENT DOCUMENTS 5,171,249  12/1992  Stefanchik et al. .................. 606/142
5,514,149   5/1996  Green et al. ......................... 606/158

FOREIGN PATENT DOCUMENTS

WO 97/39689  10/1997  WIPO ........................... A61B 17/10

*Primary Examiner*—Michael Buiz
*Assistant Examiner*—Julian W. Woo
*Attorney, Agent, or Firm*—Richard L. Myers

[57] ABSTRACT

A surgical clip applier for use in applying ligation as well as fixation surgical clips or fasteners to a vessel or other tissue at a surgical site. The clip applier includes an elongated hollow outer body having a proximal end attached to an actuating mechanism and a distal end. A pair of generally opposing jaws are coupled to the distal end of the outer body and are configured with guide slots for receiving a surgical clip. Means are provided for advancing a clip from within the outer body into the guide slots. Movement of the actuating mechanism moves the jaws between an open position, a first closed position and a second and fully closed position. The jaws are placed over a section of tissue and closed to the first closed position such that the tissue is compressed. The clip site is tested for proper ligation, and if acceptable, a clip is advanced into the jaw members. A pair of shims are moved distally within the elongated outer body and inserted between the guide slots and the clip such that the clip is compressed over the tissue. The jaws are then moved to the second closed position to fully compress the clip over the tissue and the shims withdrawn. A V-shaped surgical clip of the present invention is provided in a semi-closed configuration to minimize the required overall outer diameter or width of the surgical clip applier.

31 Claims, 3 Drawing Sheets

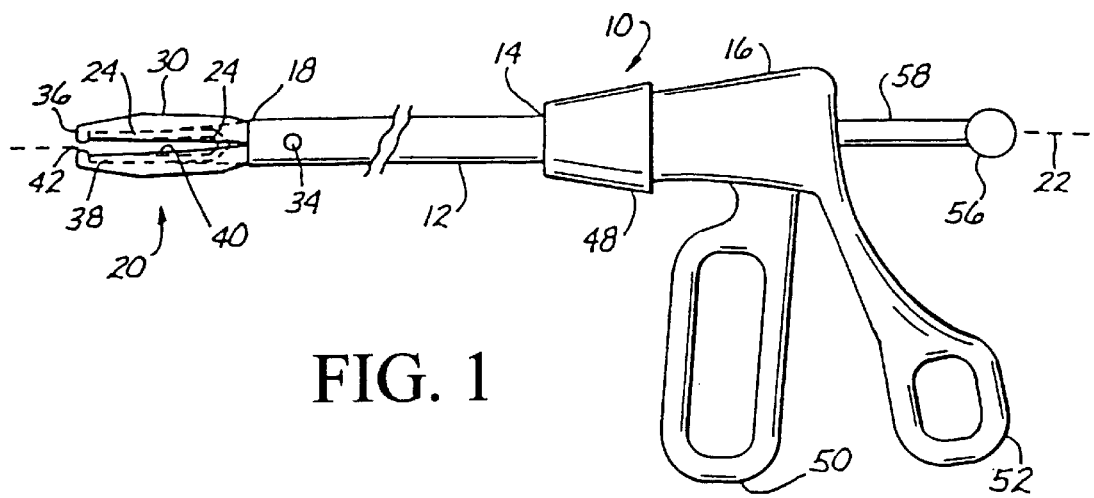
FIG. 1
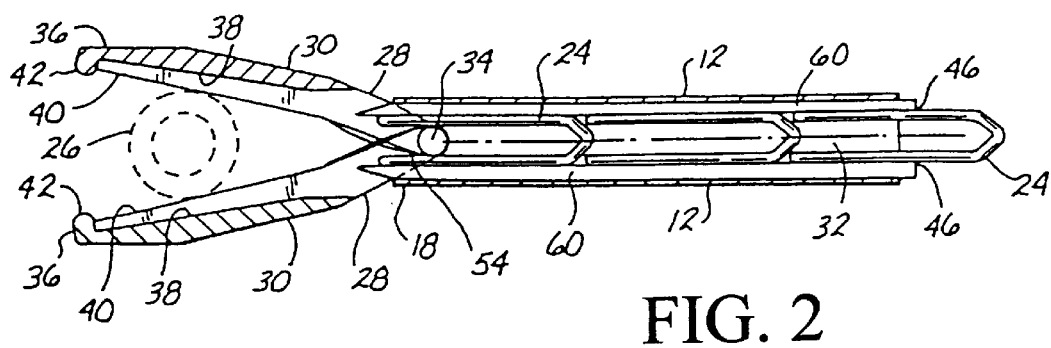
FIG. 2
FIG. 3
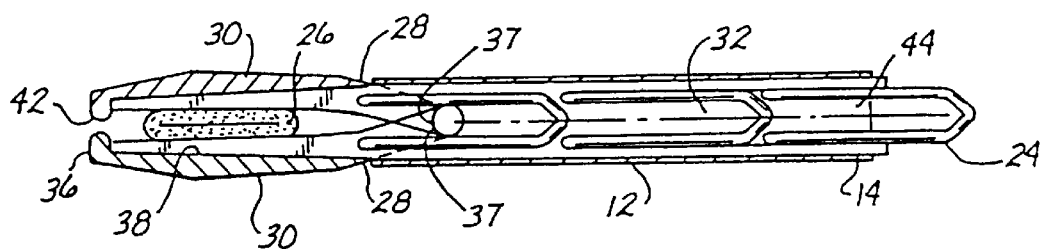

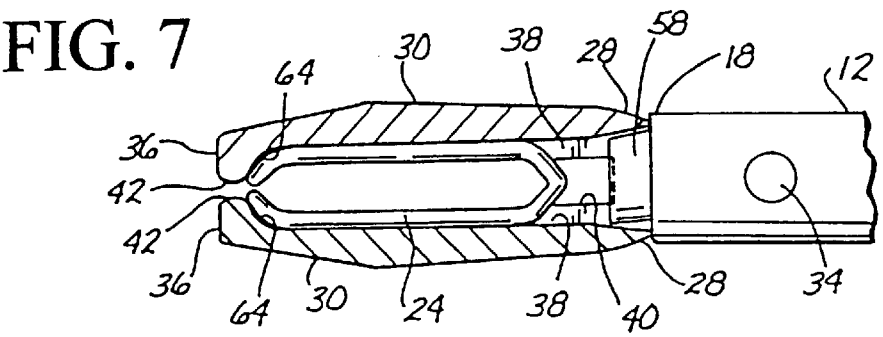
FIG. 7
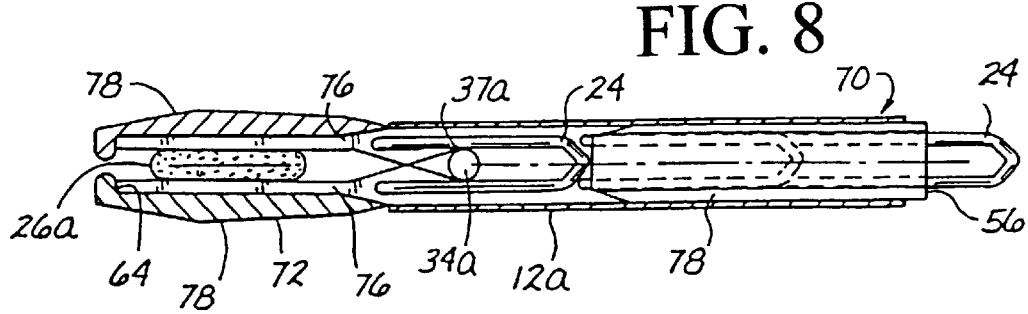
FIG. 8
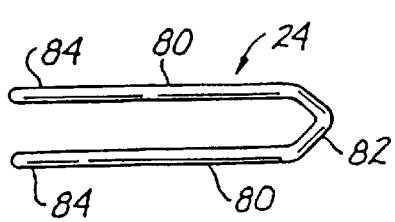
FIG. 9a
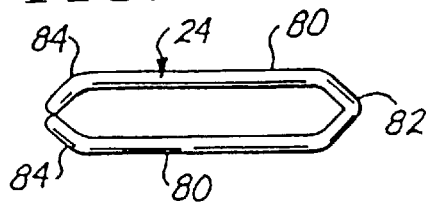
FIG. 9b
FIG. 9c

GRASPING CLIP APPLIER

RELATED APPLICATIONS

This application claims the benefit of U.S. Provisional Application No. 60/015,625, filed Apr. 19, 1996. This application is also related to U.S. patent application Ser. No. 08/278,705, entitled *MALLEABLE SURGICAL CLIP APPLIER AND METHOD,* filed on an even date herewith, which is expressly incorporated herein by reference.

FIELD OF THE INVENTION

This invention relates generally to surgical clip appliers and surgical clips and, more particularly, to an improved surgical clip applier and method for applying multiple surgical clips.

BACKGROUND OF THE INVENTION

Endoscopic surgical techniques, including laparoscopic and arthroscopic techniques, are gaining wide acceptance and are being increasingly used. There are many benefits associated with these minimally invasive techniques, which include, reduced patient trauma, reduced risk of post-operative infection and reduced recovery time.

Various types of surgical instruments have been developed for use with these endoscopic surgical techniques and procedures, including clip appliers for the occlusion and ligation of vessels as well as other conduits and tissue structures.

Conventional clip appliers, as currently used in these endoscopic procedures, typically consist of an elongate body having a proximal end connected to an actuating mechanism and a pair of clip compressing devices or jaws supported at the distal end. In one configuration, the jaws typically consist of a pair of opposing jaw members which are movable with respect to each other. Each of the jaw members may include a slot or other means for retaining an associated leg of a surgical clip. In this configuration, the jaws are moved relative to each other when a surgeon operates an actuating handle coupled to the actuating mechanism. In some appliers, multiple surgical clips are supported in the elongate body and moved distally, one at a time, into the jaw members in preparation for being applied to a section of tissue.

A conventional ligating clip typically includes a pair of symmetrical legs connected to an apex. The legs may extend outwardly from the apex to form a U or V-shaped clip. In use, the legs are passed over the desired section of tissue and then compressed to clip onto the tissue.

There are several deficiencies associated with the conventional clip appliers as described and as currently used. For instance, when using a conventional clip applier in an endoscopic procedure, the elongated body, or alternatively, the jaws are loaded with at least one open surgical clip in preparation for surrounding the vessel or other tissue. The jaws are then closed and the clip applier inserted through a trocar cannula so that the clip may be positioned adjacent the vessel or other tissue. The jaws are then opened and the clip compressed onto the vessel or tissue.

The size of the vessel or tissue to be clipped is limited by the size of the available clip. In general, a larger vessel or section of tissue requires a larger clip. However, since the clip applier must pass through the cannula of the trocar, its overall outer diameter must be less than that of the cannula. Also, since the clips are typically stored within the elongate body, the overall outer diameter of the clip applier may limit the size of the clips. Thus, there is a need for a clip applier which can be used with conventional trocars but which is not limited to conventional sized clips.

Another deficiency associated with conventional clip appliers is the inability to test a proposed clip site or clip location. For example, it would be beneficial to know whether a given section of tissue will actually occlude or properly ligate when clipped, without actually applying a clip to that section of tissue. There is also a need for such a clip applier and associated surgical clip which is simple to operate and relatively inexpensive to manufacture.

SUMMARY

The present invention overcomes these problems of the past by providing a clip applier that is capable of containing a plurality of surgical clips and is insertable through a cannula or other small opening in the patient while being maintained with a minimum diameter cross-sectional configuration. By using surgical clips that are generally pre-compressed, the overall diameter or width of the elongate outer body may be minimized in order to facilitate insertion through a trocar. This use of pre-compressed clips also allows the use of a much larger clip for a given elongated outer body outer diameter or width, thus greatly increasing the size of vessels or other tissues which may be clipped while using a conventionally sized cannula.

The present invention also satisfies the need for a clip applier which allows a surgeon or other user to test a clip location prior to actually applying the clip. This is accomplished by closing the jaw members around a proposed section of tissue and compressing the tissue without applying a clip. This is possible since the clip may be maintained in the elongate outer body of the clip applier rather than the jaws while the surgeon performs any variety of desired tests. Once the section of tissue is deemed acceptable, the surgeon advances a clip forwardly into the jaws and around the compressed tissue.

The present invention also satisfies the need for a clip applier which allows a surgeon to control the closure or compressive force applied to a clip. By providing closure control, this clip may be applied without over-compressing the tissue. This closure control is accomplished by using pre-compressed clips which are placed over a section of tissue which has been compressed by the jaws without need for any compression of the clip. However, the clip applier of the present invention allows a surgeon or other user to further compress the clip if desired, by further actuating the jaw members.

The present invention is generally directed to an improved clip applier for applying a surgical clip or plurality of clips having outwardly extending legs to occlude, ligate or otherwise clip a vessel or other section of tissue. Broadly speaking, an embodiment of a clip applier according to the present invention includes an elongated outer body which defines a longitudinal axis between a proximal end and a distal end. An actuating mechanism is connected to the proximal end and an operating assembly is positioned at the distal end.

The operating assembly includes a pair of generally opposing jaw members which extend distally away from the elongated outer body. Each jaw member includes an internal guide slot which extends longitudinally along an inner surface. The guide slots are configured for receiving the surgical clip. Each of the jaw members is pivotally coupled to the outer body.

The actuating mechanism is attached to the outer body and coupled to the jaw members such that actuation of the actuating mechanism moves the jaw members between an open position, a first closed position and a second closed position. In the open position, the jaw members are oriented apart from each other such that a vessel or other section of tissue may be easily captured between them. In the first closed position, the jaw members are moved or pivoted towards each other such that the inner surfaces are generally parallel to each other. In this configuration, a vessel or other section of tissue held between the jaw members is compressed. In the second closed position, the jaw members are further moved to the fully closed position such that each of the inner surfaces is in contact with the respective other and the section of tissue held between the jaw members is further compressed.

In another aspect of the present invention, the operating assembly further includes a pair of protruding lip portions. Each of these lip portions extends inwardly from the distal end of each jaw member. The guide slots terminate distally within each jaw member and form a smooth transition into the lip portion. This smooth transition tapers inwardly to create a forming feature for shaping a clip which is moved distally from the outer body and into the guide slots.

In yet another aspect of the present invention, a second actuating mechanism is coupled to the proximal end of the elongate outer body. This second actuating mechanism is coupled to a push rod which extends substantially coaxially through the outer body to contact the surgical clip. Distal movement of the second actuating mechanism by a surgeon forces a clip distally from within the outer body and into the guide slots of the jaw members. A track or slot is provided for guiding the surgical clip within the outer body. The track is configured for supporting a plurality of surgical clips such that a number of clips may be advanced and applied sequentially.

The surgical clip of the present invention may include a first leg, a second leg and a generally V-shaped base which is connected to each of the first and second legs. The legs extend outwardly from the base in a spaced apart and parallel fashion. Each of the legs includes a weakened point or notch adjacent the distal end. This weakened point reduces the force necessary to shape or form the clip as it is moved forwardly into the guide slots and encounters the forming curve or other structure.

In another embodiment of the present invention, a clip applier for applying a surgical clip to a section of tissue within a patient includes an elongate hollow outer body having a proximal end and a distal end. The proximal end is attached to an actuating mechanism having an actuating handle.

An elongate inner member, which also has a proximal end and a distal end, is movably mounted coaxially within the outer body. The inner member, which includes an axial passageway for receiving a plurality of surgical clips, is coupled to the actuating assembly at its proximal end and extends distally through the outer body. This inner member is slidably movable within the outer body by actuation of the actuating mechanism.

An operating assembly is coupled to the distal end of the inner member and includes a pair of generally opposing jaw members. Each jaw member has a guide slot for receiving the clip as it is moved distally from within the inner member as previously described. In addition, each of the guide slots transitions into an inwardly protruding lip portion at the distal end of each jaw member as previously described.

An elongated shim member may be mounted within the outer body for retractable insertion into the guide slots. The shim may be extendable between a clip mounted within the guide slots and at least one of the guide slots. Thus, by extending the shim into a guide slot, the clip may be compressed and the legs bent inwardly.

The actuating mechanism is coupled to at least one of the jaw members and is actuable to move the jaws members between an opened and at least one closed position. The actuating mechanism includes a main body which is attached to the proximal end of the outer body, and an actuating handle which is movably coupled to the main body. The actuating handle is connected to the proximal end of the inner member such that movement of the handle in relation to the main body forces the inner member to move relative to the outer body and thus, the jaw members to pivot relative to each other. Further actuation of the handle moves the shim within the elongate outer body for compressing the clip. A second actuating mechanism, which is also coupled to the outer body, includes a push rod for moving at least one clip distally from within the inner member into the guide slots of the jaw members.

A preferred method of applying a surgical clip to a vessel or other section of tissue in a patient according to the principles of the present invention comprises the steps of providing a clip applier which includes an elongated body containing at least one clip and having a proximal end attached to at least one actuating mechanism. An operating assembly is supported at the distal end of the elongated body and includes a pair of opposing jaw members which are operable between an opened, a first closed and a second closed position. Each jaw member further includes a guide slot along an opposing inner surface for receiving a clip. The guide slot is sufficiently deep such that a clip may be moved distally from within the elongated body to within the slots while the operating assembly is in the first closed position. The clip applier is then positioned within a patient such that the operating assembly is adjacent the section of tissue to be clipped. The jaw members are then opened.

The clip applier may then be manipulated such that the jaw members are passed over and generally surround the desired section of tissue. The jaw members are then moved to a first closed position such that the section of tissue is grasped and compressed within the jaw members. A clip is then moved distally into the guide slots of the jaw members after moving the jaw members to the first closed position such that the clip substantially surrounds the compressed section of tissue. The clip applier is then withdrawn from the section of tissue such that the clip remains on the tissue. The clip applier is then removed from the patient.

In another aspect of the present invention, the method includes the step of moving the jaw members to a second closed position such that the jaw members are moved further inwardly. This step compresses the clip over the section of tissue.

In yet another aspect of the present invention, the method includes testing the grasped section of tissue prior to moving the clip distally into the jaw members. During this step, a surgeon may check for proper occlusion, ligation, clip location or any other aspect related to grasping, compressing or clipping a section of tissue, prior to actually applying the clip. If the grasped section of tissue is deemed not desirable, the jaws may be moved to the open position and the clip applier moved to surround a new section of tissue. In this way, the surgeon may pre-confirm that ultimate placement of the clip will accomplish the desired objectives.

This invention, together with the additional features and advantages thereof, which is only summarized in the foregoing passages, will become more apparent to those of skill in the art upon reading the description of the preferred embodiments, which follows in the specification, taken together with the following drawings.

BRIEF DESCRIPTION OF THE DRAWINGS

FIG. 1 is a side view of an embodiment of a clip applier according to the principles of the present invention.

FIG. 2 is a cross-sectional view of the clip applier as depicted in FIG. 1 taken along lines 2—2 and shown in the open position adjacent to a section of tissue.

FIG. 3 is a cross-sectional view illustrating the clip applier as depicted in FIG. 2 shown in the first closed position.

FIG. 7 is a partial cross-sectional view of a clip applier according to the principles of the present invention shown having a forming curve in each guide slot.

FIG. 8 is a partial cross-sectional view of a second alternative embodiment of a clip applier according the principles of the present invention shown in the first closed position.

FIG. 9a is a side view of a surgical clip according to the principles of the present invention.

FIG. 9b is a side view of the surgical clip as illustrated in FIG. 9a which has been formed within the guide slots of the jaw members according to the principles of the present invention.

FIG. 9c is a side view of the surgical clip as illustrated in FIG. 9a shown fully compressed.

DESCRIPTION OF THE PREFERRED EMBODIMENTS

Figure 4:
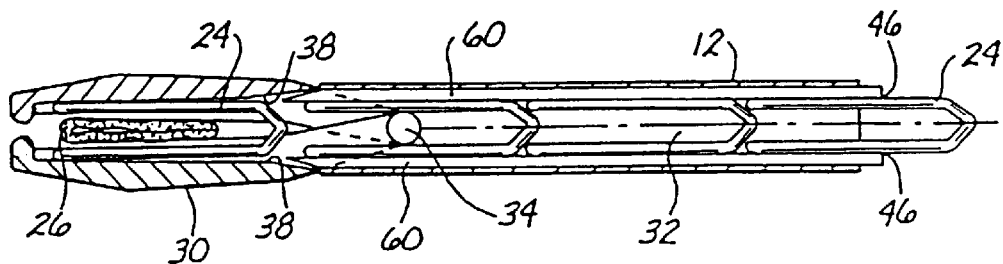
FIG. 4 is a cross-sectional view illustrating the clip applier as depicted in FIG. 3 shown with a clip inserted into the jaw members.

Referring now to the drawings, wherein like reference characters designate identical or corresponding parts throughout the several views and embodiments, a clip applier of the present invention is illustrated in FIG. 1 by reference numeral 10. As shown, the clip applier 10 of the present invention includes an elongate outer body 12 having a proximal end 14 connected to an actuating mechanism 16 and a distal end 18 coupled to an operating assembly 20. A longitudinal axis 22 is generally defined along the outer body 12. A surgical clip 24 is shown within the operating assembly 20.

The outer body 12 which may be an elongated rigid shaft, extends between the proximal end 14 and the distal end 18 and includes an axial passage therebetween. The outer body 12 may be made from a variety of rigid biocompatible materials, such as stainless steel, a plastic such as acrylonitrile-butadiene-styrene (ABS), a polycarbonate material or any other biocompatible material capable of the requirements described herein. In a preferred embodiment, the outer body 12 is rigid, however it may also be made from a semi-compliant or flexible material to allow some flexibility along the axis 22.

Preferably, the elongated outer body 12 comprises a tubular shaft having a relatively small outer diameter for insertion into and through a trocar cannula or other small incision. The outer body 12 preferably has a wall thickness sufficient to support the operating assembly 20, its operation and any required manipulation within a patient. In a preferred embodiment, the elongate body has a round cross-section, but any cross-section may be used and an oval or clip-shaped cross-section may be beneficial. In the illustrated embodiment, the outer body 12 has an outer diameter of approximately 5 mm. However, other diameters may also be used and which are preferably minimized considering the size of the surgical clip 24 maintained within. Since the overall outer diameter or width of the outer body 12 is limited in size by the inner diameter of the trocar through which it must pass, minimizing this outer diameter while maximizing the clip 24 size is of great importance.

The proximal end of the elongated outer body 12 may be rigidly secured to the actuating mechanism 16 such that the clip applier 10 is a generally structurally rigid device. Thus, the proximal end 14 may be attached to the actuating mechanism 16 using any of a wide variety of methods available and known to those of skill in the art. As an example, the proximal end 14 may be attached to the actuating mechanism 16 through welding, the use of adhesives, fasteners or a threaded fitting or similar.

The distal end 18 of the elongated outer body 12 may be coupled to the operating assembly 20 to provide structural support as well as for actuating the operating assembly 20 between an open position and at least two closed positions. In a preferred embodiment, the elongated outer body 12, which may be a hollow tubular member, is not directly attached to the operating assembly 20 but is operatively removable relative to it. Preferably, the operating assembly 20 is moved into and out of the distal end 18 by operation of the actuating mechanism. In this configuration, the distal end 18 is moved relative to, and contacts a tapered or cammed outer surface 28 on opposing sides of the operating assembly 20 such that the operating assembly 20 is moved between an open position and a second or fully closed position.

Referring now to FIGS. 2–6, the clip applier 10, and more specifically the operating assembly 20, will be described in greater detail. The operating assembly 20 may include a pair of generally opposing jaw members 30 which extend distally from the distal end 18 of the outer body 12. In a preferred embodiment, each of the jaw members 30 is coupled to an elongated inner member 32 through a pivot axis 34 and more preferably a pair of spaced-apart pivot axes 34. Alternatively, each of the jaw members 30 may extend from a separate pivot axis. Another configuration contemplates one of the jaw members 30 being fixed with the other pivotable.

Figure 5:
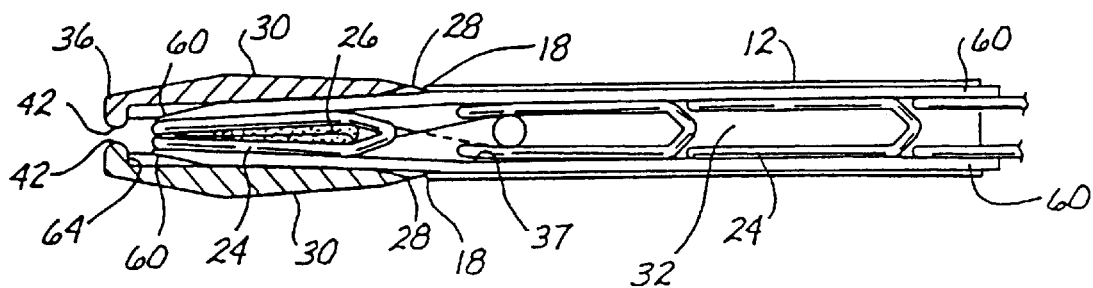
FIG. 5 is a cross-sectional view illustrating the clip applier as depicted in FIG. 4 showing a pair of shims extending into the guide slots.

Each of the jaw members 30 extends distally from the pivot axis 34 to a distal end 36. Preferably, the proximal end 14 of each jaw member 30 is configured with a clevis or bore 37 for attachment to the pivot axis 34. Each jaw member 30 includes a guide slot 38 which extends longitudinally along the interior or inner surface 40 of each jaw member 30. Preferably, each guide slot 38 extends from a proximal point on the inner surface 40 distally, terminating at the distal end 36. The guide slots 38 may be tapered such that the depth of the slot 38 decreases distally. Alternatively, the inner surface 40 may be tapered such that when the jaw members 30 are in a first closed position, they form a generally V-shaped opening as shown in FIGS. 3–5. However, both the guide slots 38 and the inner surface 40 may be relatively taper-free such that they are generally parallel when the jaw members 30 are in the first closed position as shown in FIGS. 7 and 8.

The guide slots 38, which may be aligned such that they generally oppose each other, are configured to receive the surgical clip 24 advanced from within the outer body 12, or more preferably, the inner member 32. Thus, the guide slots 38 are aligned with the clips 24 supported within the outer body 12 and more specifically, in the inner member 12.

Figure 6:
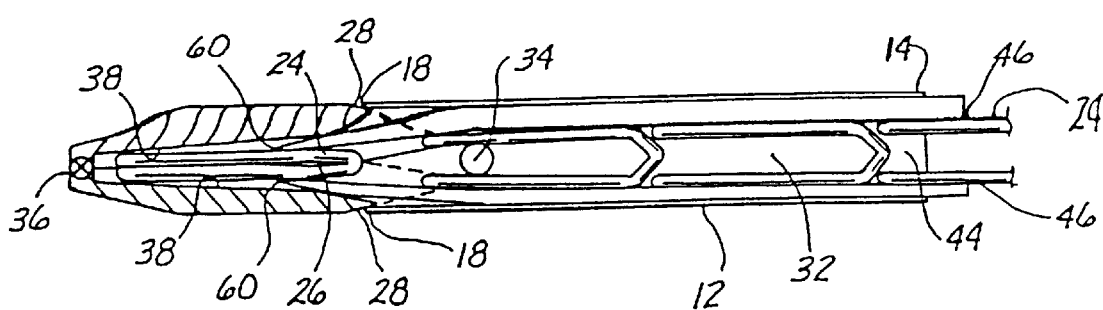
FIG. 6 is a cross-sectional view illustrating the clip applier as depicted in FIG. 5 shown with the shims being retracted.

The distal end 36 of each jaw member 30 may be provided with an inwardly protruding lip portion 42. In a preferred embodiment, the lip portion 42 on each jaw member 30 is offset such that the lip portions 42 overlap or otherwise mesh when the jaw members 30 are in the fully closed position as shown in FIG. 6. The lip portion 42 may be configured such that a vessel or other section of tissue 26 may be grasped and otherwise captured within the jaw members 30. Each lip portion 42 may be rounded and provided with a smooth outer surface such that any potential damage to tissue 26 is minimized. In a preferred embodiment, each lip portion 42 forms a smooth curved path and transition into each of the guide slots 38 at the distal end 36.

This smooth curved path may be configured for shaping or otherwise bending the distal end of a clip 24 that is advanced into the guide slots 38. In this configuration, the smooth curved path may be a forming curve 64 within each guide slot. In a preferred embodiment, this forming curve may be an inwardly tapering portion or curved transition into the lip portion 42 as shown in FIG. 7. In the drawing, the forming curve 64 bends the distal portion of each clip 24 as it is forced into the guide slots. These formed bends may be used to prevent the clip from coming off of the vessel or other tissue 26.

Each jaw member 30 may be a generally symmetrical part with the exception of the pivot clevis or bore 37 which may be somewhat unsymmetrical to insure proper alignment with the spaced apart pivot axes 34. However, jaw members 30 may be provided which are identical (symmetrical) but which do not pivot from a common pivot axis 34; or alternatively jaw members 30 may be provided which are asymmetrical. In another configuration, one jaw member 30 is generally fixed while the remaining jaw member 30 pivots relative to the fixed one. Preferably, the jaw members 30 are configured such that their overall outside diameter or maximum width is smaller than that of the elongated outer body 12 when maintained in the fully closed position as shown in FIG. 6.

The elongate inner member 32 is provided to facilitate actuation of the operating assembly 20. This inner member 32 preferably includes a proximal end 44 which is coupled to the jaw members 30 through pivot axes 34. The inner member 32 is preferably a shaft, sleeve, or other tubular member similar to the outer body 12 but of a smaller maximum diameter such that it is slidable within the outer body 12 by actuation of the actuating mechanism 16.

The elongate inner member 32 may be provided with a track 46 for guiding a plurality of surgical clips 24. The track 46 which may merely describe the internal configuration of the inner member 32 is used for supporting the surgical clips 24 in a linear fashion such that the clips 24 may be slidably moved or advanced distally from within the inner member 32 and into the guide slots 38 of the jaw members 30. Thus, the track 46 may include a pair of rails, grooves, slots or any other form of guide for directing surgical clips 24 along a tubular shaft. Alternatively, the cross-section of the elongated inner member 32 may be oval or be formed such that a natural track is made. The track 46 distally terminates adjacent and aligns with the guide slots 38. In this way, surgical clips 24 advanced along the track 46 are forced into the guide slots 38. Preferably, the track 46 is aligned along the longitudinal axis 22 of the elongated outer body 12.

The actuating mechanism 16 may include any device which moves the operating assembly 20, or more preferably the elongated inner member 32, relative to the elongated outer body 12. As shown in FIG. 1, the actuating mechanism 16 may include a main body 48 which is connected to the elongated outer body 12 as previously disclosed.

An actuating handle 50 may be movably coupled to the main body 48 and linked or connected to the elongated inner member 32. In this fashion, when the handle 50 is moved relative to the main body 48, the elongated inner member 32 is moved within and relative to the elongated outer body 12. More specifically, when the handle 50 is moved rearwardly into a fixed handle or other fixed position on the main body 48, the elongated inner member 32 is extended outwardly or distally relative to the elongated outer body 12. This action advances or pushes the jaw members 30 distally or outwardly from the distal end 18 of the elongated outer body 12.

As the jaw members 30, and more specifically the pivot axis 34, is advanced distally and out of the hollow elongated outer body 12, the tapered or cammed outer surface 28 on each jaw member 30 contacts and slides against the distal end 18 of the outer body 12. A first biasing spring 54 may be used to maintain the jaw members 30 in the open position as shown in FIG. 2. This first biasing spring 54, which may be a coiled spring wire mounted between the opposing jaw members 30 as shown, is used to maintain a constant laterally outward force against the opposing jaw members 30. However, any method of maintaining the jaws open in conjunction with the actuating mechanism 16 may be used as is known to those of skill in the art of similar devices.

Conversely, moving the actuating handle 50 distally or away from the fixed handle 52 of the main body 48, retracts the elongated inner member 32 relative to the outer body 12 and forces the jaw members 30 inwardly or proximally within the distal end 18. As the jaw members 30 are drawn proximally into the generally open and hollow elongated outer body 12, the distal end 18 contacts and slides against the tapered or cammed outer surface 28 on each jaw member 30. As this cammed outer surface 28 continues to be drawn inwardly into the distal end 18 of the elongated outer body 12, the jaw members 30 are forcibly closed as shown in FIGS. 3–5. In the position shown, which is generally termed the first closed position, the vessel or section of tissue 26 may be captured and compressed within the jaw members 30. This first closed position, also allows for a surgical clip 24 to be directly passed or advanced from the track 46 into the guide slots 38.

Further actuation of the handle 50 distally or away from the fixed handle 52 of the main body 48 pushes the elongated inner member 32 further distally relative to the elongated outer body 12 and further pivots the jaw members 30 to a second or fully closed position as shown in FIG. 6. In this second or fully closed position, the jaw members 30 may be pivoted together such that each of the inner surfaces 40 contacts each other. Preferably, a substantial portion of each inner surface 40 is aligned with a similar portion of the opposing inner surface 40 to provide even compression over the vessel or section of tissue 26 grasped within. The actuating mechanism 16 may be directly coupled to the operating assembly 20 such that there is some tactile feedback in the actuating handle 50 relative to the force imparted on the jaw members 30.

A second biasing spring may be provided to maintain a continuous proximal force on the inner member 32 relative to the elongated outer body 12. In this way, the jaw members 30 may be maintained in a normally closed position, and preferably, maintained normally in the second or fully closed position as shown in FIG. 6. In this way, the overall outer diameter or maximum width of the clip applier 10 is maintained in a normally minimized state. In addition, this configuration allows the clip applier 10 to be inserted through a cannula, trocar or other small opening within a patient and manipulated to a surgical site without the need for any actuation or other operation by the surgeon. The second biasing spring may be disposed within the outer body 12 or within the actuating mechanism 16. In general, the second biasing spring may be located in any position where it may facilitate maintenance of the jaw members 30 in a normally fully closed position as shown in FIG. 6. Alternatively, the second biasing spring may be omitted and another method of maintaining the jaw members 30 in a normal position may be used. Such methods may include ball and detentes, frictional resistance or any other method as is known to those of skill in the art. In yet another alternative configuration, the jaw members 30 may be maintained in a normally open state as shown in FIG. 2.

A second actuating mechanism 56 may be provided within the elongated inner member 32 to provide a distal or forwardly applied force on the proximal most surgical clip 24. In this way, the second actuating mechanism 56 may be moved distally within the elongated inner member 32 to contact the proximal portion of the clip 24 and force the clip 24 to advance distally within the track 46. When supplied with a plurality of clips 24 the second actuating mechanism 56 advances the proximal most clip 24 distally which in turn advances the plurality of clips 24 such that the distal most clip 24 is advanced or moved forwardly into the guide slots 38 of the jaw members 30. In a preferred embodiment, the second actuating mechanism 56 includes an elongated push rod 58 which extends substantially coaxially through the inner member 32 and contacts at least one clip 24 at its base or distal end.

The second actuating mechanism 56 may be provided for moving the push rod relative to the elongated inner member 32. This preferred second actuating mechanism 56 which may include a second actuating handle coupled to the main body 48, generally forces the push rod 58 in a linear fashion coaxial with the longitudinal axis 22. A biasing spring may be provided to maintain the push rod 58 in either the distally extended position or in a retracted position. It is preferred that the second actuating mechanism 56 be coupled to the first actuating mechanism 16 such that a surgeon may advance a surgical clip 24 into the guide slots 38 when the jaw members 30 are in the first closed position (FIGS. 3–5). However, the surgeon is preferably allowed the opportunity to close the jaw members 30 to the first closed position without having to advance a clip 24 (FIG. 3). In an alternative configuration, the push rod 58 is coupled to the second actuating mechanism 56 using a ball and detent or similar system. This allows a surgeon to appropriately advance the push rod 58 for each clip 24. It is understood that many varieties and configurations of actuating mechanisms may be used to operate the operating assembly 20 as well as the push rod 58. Any of these configurations, which will be understood to those of skill in the art, may be substituted for the above described actuating mechanisms.

In addition to actuating the jaw members 30, the actuating mechanism 16 is preferably coupled to a shim 60 which extends distally through the elongated outer body 12 to the operating assembly 20. The shim 60 which preferably includes a pair of elongated shims 60 may be movably supported within opposing sides of the elongated outer body 12. Each shim 60 may be extendable into an associated guide slot 38. The shim 60, which may comprise an elongate tubular member slidable over the inner member 32 and within the outer body 12 and having a pair of protruding portions or shims which may be extended into the guide slots 38, is used to compress the surgical clip 24 over a vessel or other section of tissue 26. The shim 60 is extended distally such that it is inserted between the guide slots 38 and the legs of a surgical clip 24 placed within the jaw members 30. In this way, the shim forces the clip 24 laterally inwardly where it is thus compressed.

In a preferred embodiment, the shims 60 are coupled to the actuating mechanism 16 and are advanced or extended distally into the guide slots 38 when the actuating handle 50 is fully moved distally, thus closing or otherwise moving the jaw members 30 to the second or fully closed position. When used with tapered guide slots 38 as previously discussed, the compressive force applied to the clip may be unevenly distributed or alternatively evenly distributed.

Referring now to FIG. 8, an alternative embodiment of a clip applier 70 according to the principles of the present invention will be described, wherein like elements to those illustrated in FIGS. 1–5 are designated by like reference numerals followed by the letter "a". In this embodiment, the clip applier 70 includes an operating assembly 72 which may be coupled to an elongated outer body 12a and actuated in a manner similar to that described for the previous embodiment. However, in this embodiment, each of the jaw members 74 includes a modified guide slot 76. Each guide slot 76 is configured such that it defines a smooth and direct path generally parallel to the longitudinal axis 22a. In this embodiment, neither of the guide slots 76 includes a taper along a substantial portion of its length. The clips 24a advanced into the guide slots 76 are compressed by actuating the jaw members 72 into the second or fully closed position. There are no shims or other compression elements in this embodiment, and thus no need for tapered guide slots 76. A push rod 78 may be provided to incrementally advance each clip 24a into the guide slots 76.

Referring now the FIGS. 9a–9c, the surgical clip 24 may be U-shaped or V-shaped with a pair of generally opposed legs 80. An intermediate portion or base 82, which for purposes of this invention includes a U-shaped, V-shaped, or any similarly shaped base, interconnects the respective legs 80. The clip 24 may be made from most any cross-sectional shape or plurality of shapes, however, a rectangular or even a square cross-section is preferred.

The clip 24 may be made from a malleable material which allows it to become compressed or closed through actuation or closure of the jaw members 30. Thus, the material may include any biocompatible material which is bendable and maintains sufficient strength such that is may occlude or otherwise clip a section of tissue. Such a clip 24 may be made from a titanium, alloys of titanium, or a stainless steel. However, other materials may also be used as are known by those of skill in the art.

In a preferred embodiment, the clip 24 includes a generally V-shaped base portion 82 interconnecting a pair of legs 64. These legs may extend outwardly in a parallel fashion. In a preferred embodiment, the clips 24 are supplied with the legs 80 in a pre-compressed or semi-closed configuration as shown. This configuration allows the outer overall diameter of the inner member 32, and thus the outer body 12, to be minimized. The clip applier 10 advantageously uses the clips 24 by compressing the vessel or other section of tissue 26 prior to applying the clip. Thus, the clip applier 10 may be supplied as a very narrow or low profile instrument having jaw members 30 that may be urged open to a great angle with respect to each other to capture large vessels or other large sections of tissue 26 without having to support large clips.

In a preferred embodiment, each leg 82 may include a weakened point 84 permitting the leg 82 to be more easily formed or otherwise bent about the weakened point 84. For example, when advancing the clip 24 into guide slots 38 having a smooth transition or forming feature 64 as shown in FIG. 7. The weakened point 84, which may be a notch, groove, pre-bent location or any other structure for reducing the force required to form or otherwise bend the clip 24 is preferably located adjacent the distal end of each leg 80 as shown in FIGS. 9a and 9b.

Referring now to FIGS. 1–6, a method of using the clip applier 10 in an endoscopic surgical procedure (which includes laparoscopic as well as arthroscopic procedures for purposes of this disclosure) will be described. Initially, the surgical clip 24 (or a plurality of the clips 24) is loaded or otherwise inserted into the track 46. The clip applier 10 is then placed in its normal or retracted configuration such that the jaw members 30 are fully closed as previously described. In this configuration, the diameter or overall cross-sectional area of the clip applier 10 is minimized. This allows insertion into a cannula (not shown) of minimal diameter or other small opening while supplying a surgical clip 24 of relatively large size. In fact, a clip 24 having legs 80 of most any length may be used. The legs 80 are only limited by the length of the guide slots 38.

The clip applier 10 may then be manipulated and positioned within the patient such that the closed jaw members 30 are moved adjacent the section of tissue 26 to be clipped. The jaw members 30 are then opened using the actuating mechanism 16. With the jaw members 30 open, the clip applier 10 is manipulated such that the jaw members 30 pass over and generally surround the desired section of tissue 26. The jaw members 30 are then moved to a first closed position as shown in FIGS. 3–5. In this first closed position, the section of tissue 26 is compressed and the surgeon may test the clip site for appropriateness. In other words, the surgeon may test a clip location prior to actual placement of the clip 24 either in the closed jaw members 30 or around the section of tissue 26. In this way, the surgeon may select a preferable or improved section of tissue 26 to be clipped. This testing may include checking the vessel or tissue 26 for appropriate occlusion, ligation, ease of access to the clip location, or any other test as is known to those of skill in the art.

Once an appropriate section of tissue 26 has been selected and grasped within the closed jaw members 30 positioned at a first closed position, a clip 24 may be moved distally into the guide slots 38 of the jaw members 30 such that the clip 24 substantially surrounds the compressed tissue 26. At this point, the clip applier 10 may be removed from the patient leaving the uncompressed clip 24 on the uncompressed section of tissue 26.

Alternatively, the surgeon may prefer to compress the clip 24 over the section of tissue 26. This step of compressing the clip 24 may include moving at least one of the shims 60 distally within the outer body 12 such that it is inserted between a guide slot 38 and the clip 24. In this way, the clip 24 is forced inwardly and compressed over the section of tissue 26.

Further compression of the clip may be achieved by moving the jaw members 30 to the second or fully closed position with the shim extended and remaining in the guide slot 38. Preferably, this step includes inserting one of the shims 60 into each of the guide slots 38 and retracting the shims 60 from within the guide slots 38 while moving the jaw members 30 the second or fully closed position. Moving the jaw members 30 to the fully closed position while retracting the shims 60 provides even compression of the clip 24 over the section of tissue 26 as is shown in FIG. 6. The jaw members 30 may then be opened from around the tissue 26 such that the clip 24 is released from the jaw members 30 and left remaining and clipped to the section of tissue 26. The clip applier 10 may then be withdrawn and removed from the patient.

In yet another broad aspect of the present invention, the method includes the step of actuating a second actuating mechanism 56 to move an elongated push rod 58 distally within the elongated inner member 32. Distally extending the push rod 58 forces the clip 24 to move distally along the track 46. This step forces the distal most clip 24 into the guide slots 38.

It will be understood that various modifications can be made to the various embodiments of the present invention herein disclosed without departing from the spirit and scope thereof. For example, various sizes of the clip applier and clip are contemplated as well as various types of construction materials. Also, various modifications may be made in the configuration of the parts and their interaction. Therefore, the above description should not be construed as limiting the invention, but merely as an exemplification of preferred embodiments thereof. Those of skill in the art will envision other modifications within the scope and spirit of the present invention as defined by the claims appended hereto.

What is claimed is:

1. An endoscopic clip applier for applying a surgical clip to at least one object in a surgical procedure, said clip applier comprising:

an elongated hollow outer body having a proximal end and a distal end;

an elongated inner member having a proximal end, a distal end, and an axial passageway, said inner member being slidably disposed in said outer body;

a first actuating mechanism connected to the proximal end of the outer body and the proximal end of the inner member, the actuating mechanism being operable to slide the inner member within the outer body;

a surgical clip disposed in the axial passageway of the inner member;

an operating assembly coupled to the distal end of the inner member and including a pair of opposing jaw members each having a guide slot for receiving a clip as it is moved distally from within the axial passageway of the inner member, each of said guide slots transitioning distally into a progressively inwardly protruding lip portion; and a second actuating mechanism coupled to said outer body for moving the clip from the axial passageway of said inner member into said guide slots and toward the progressively inwardly protruding lip portions.

2. The clip applier as recited in claim 1, wherein:

the clip has a first leg and a second leg; and at least one of said first leg and said second leg of the clip has a point of weakness.

3. The clip applier as recited in claim 2 wherein at least one of said first leg and said second leg has a substantially rectangular cross section.

4. A method of applying a surgical clip to at least one object in a surgical procedure using an endoscopic clip applier including an elongate body having an actuating mechanism connected to a proximal end and a pair of opposing jaw members positioned at a distal end, each jaw member having a guide slot for receiving a clip from within the elongate body, said method comprising the steps of:

positioning the clip applier within the patient such that the jaw members are adjacent the object to be clipped;

opening the jaw members;

orienting the clip applier such that the jaw members pass over the tissue;

manipulating the jaw members to move the object to a compressed state within the jaw members; and following the manipulating step, advancing the clip distally into the slots of the jaw members to an operative position over the object in the compressed state to maintain the object in the compressed state; and after the first advancing step, locking the clip in the operative position with the object in the compressed state.

5. The method of applying a surgical clip as recited in claim 4 wherein prior to the compressing step, the method includes the step of testing the clip location on the object.

6. The method of applying a surgical clip as recited in claim 4 wherein the step of compressing comprises moving the shim distally within the elongated body and into at least one of the guide slots such that the clip is compressed onto the object.

7. The method of applying a surgical clip as recited in claim 6 and further comprising the step of:

retracting the shim from the guide slots; and moving the jaw members to compress the clip and further compress the object.

8. The method of applying a surgical clip as recited in claim 7 wherein the steps of retracting the shim and moving the jaw members to a second closed position occur substantially simultaneously.

9. The method of applying a surgical clip as recited in claim 6 wherein the step of moving the shim distally comprises moving a pair of generally opposing shims distally within the elongated body such that each shim is moved into a guide slot and compresses a leg of the clip against the tissue.

10. The method of applying a surgical clip as recited in claim 4 wherein the step of moving the clip distally comprises moving an elongated push rod distally such that the push rod forces the clip to move distally.

11. A method for applying a surgical clip to at least one object in a surgical procedure, comprising the steps of:

providing an endoscopic clip applier including an elongated body containing at least one clip and having a proximal end attached to an actuating mechanism and an operating assembly supported at a distal end, said operating assembly having a pair of opposing jaw members operable between an open position and a closed position, each jaw member having a guide slot extending along an inner surface for receiving the clip, said slots being sufficiently deep that the clip can be moved distally from the elongated body into said slots while said operating assembly is in said closed position;

positioning the clip applier adjacent the object to be clipped;

operating the operating assembly to move the jaws to the open position;

manipulating the clip applier within the patient such that the jaw members pass over and generally surround the object;

moving the jaw members to the closed position such that the object is grasped within the jaw members and moved to a compressed state; and advancing a clip distally along the guide slots of the jaw members after moving the jaw members to the closed position such that the clip substantially surrounds the object to maintain the object in the compressed state.

12. The method of applying a surgical clip as recited in claim 11 wherein the step of moving the jaw members to the closed position comprises:

moving the jaw members such that the guide slots are generally opposing and parallel to each other and define a generally straight path for a clip proximally located in said elongated body.

13. The method of applying a surgical clip as recited in claim 11 wherein prior to the advancing step the method further comprises the step of testing the grasped object for sufficient occlusion.

14. The method of applying a surgical clip as recited in claim 11 wherever the moving step includes the step of compressing the clip over the object.

15. The method of applying a surgical clip as recited in claim 14 wherein the closed position of the jaws is a first closed position and the step of compressing the clip includes the step of moving the jaw members to a second closed position such that the jaw members compress the clip over the object.

16. A surgical clip applier having a longitudinal configuration and extending between a proximal end and a distal end, the applier comprising:

an actuating mechanism disposed at the distal end of the surgical clip applier;

an operating assembly disposed at the distal end of the surgical clip applier;

opposing jaw members included in the operating assembly at the distal end, the jaws having an open state and a closed state;

portions of the applier defining a guide slot extending between the actuating mechanism at the proximal end and the operating assembly at the distal end;

a plurality of clips movably disposed in the guide slot in a predetermined configuration;

a clip advancement member operable from the proximal end of the surgical clip applier to advance at least one of the clips in the predetermined configuration into the jaws; and the jaws being in the closed state to receive the advancing clip in the predetermined configuration.

17. The surgical clip applier recited in claim 16 wherein the applier is configured such that the clip maintains the predetermined configuration during movement from the guide slot into the jaws.

18. The surgical clip applier recited in claim 17, wherein:

the clip has a pair of opposing legs; and the legs of the clip in the predetermined configuration are substantially parallel.

19. The surgical clip applier recited in claim 16 and being operable to place the clip on an object having an uncompressed state with a particular thickness and a compressed state, the clip operating to hold the object in the compressed state, wherein:

the substantially parallel legs of the clip in the predetermined configuration are separated a particular distance less than the particular thickness of the object.

20. The surgical clip applier recited in claim 19 wherein the actuating mechanism is operable at the proximal end to compress the object from the particular thickness to a second thickness less than the particular distance associated with the clip.

21. A method for applying a clip to an object in a surgical procedure, comprising the steps of:
 providing an endoscopic clip applier having an elongate body holding at least one clip, the body having a proximal end with an actuating mechanism and a distal end with a pair of opposing jaw members movable by operation of the actuating mechanism;
 compressing the object to a compressed state by moving the jaws of the applier;
 moving the clip from the body of the applier into the jaws of the applier when the object is in the compressed state; and
 removing the clip applier from the object leaving the clip to hold the object in the compressed state.

22. The method recited in claim 21 wherein the clip does not change state during the providing step, the compressing step, and the moving step.

23. The method recited in claim 22 wherein the providing step includes the step of providing the clip in a predetermined configuration with a pair of legs each extending to a free end, the legs having a generally parallel relationship.

24. The method recited in claim 23 further comprising the step of:
 crimping the free ends of the clip legs by operation of the actuating mechanism at the proximal end of the applier.

25. The method recited in claim 24 wherein the crimping step occurs during the moving step.

26. The method for applying a clip to an object in a surgical procedure, comprising the steps of:
 providing an endoscopic clip applier having an elongate body with an actuating mechanism disposed at a proximal end of the body and a pair of opposing jaw members disposed at a distal end of the body;
 storing a clip having in a stored configuration a pair of legs extending longitudinally of the body;
 compressing the object from a first thickness to a second thickness;
 moving the clip from the body into the jaws and generally around the compressed object, the clip in the jaws having a loaded configuration substantially the same as the stored configuration.

27. The method recited in claim 26 further comprising:
 removing the applier from the object with the clip disposed around the object in an operative configuration substantially the same as the loaded configuration.

28. The method recited in claim 26 wherein the storing step includes the step of providing the clip in the stored configuration with the pair of legs in a substantially parallel relationship.

29. The method recited in claim 26 wherein the providing step includes the step of:
 providing the clip in the stored configuration with the pair of legs separated along their length by a distance less than the first thickness of the object and greater than the second thickness of the object.

30. The method recited in claim 26 wherein the object is a conduit and the conduit is substantially occluded after the removing step.

31. A method for applying a clip to an object in a surgical procedure, comprising the steps of:
 providing a clip applier having an elongate body holding at least one clip, the body having a proximal end with an actuating mechanism operable by an actuating force, and distal end with a pair of opposing jaw members;
 compressing the object by operation of the jaws without moving the clip;
 advancing the clip into the jaws without changing the shape of the clip and without moving the jaws;
 during the compressing step, directing substantially all of the actuating force to compress the object; and
 during the advancing step, directing substantially all of the actuating force to advance the clip.

* * * * *